(12) United States Patent
Murakami et al.

(10) Patent No.: US 8,506,780 B2
(45) Date of Patent: Aug. 13, 2013

(54) GAS SENSOR

(75) Inventors: Mika Murakami, Nagoya (JP); Hiroki Fujita, Kasugai (JP); Sumiko Horisaka, Nagoya (JP); Takashi Ito, Kasugai (JP); Sang Jae Lee, Ama-Gun (JP)

(73) Assignee: NGK Insulators, Ltd., Nagoya (JP)

( * ) Notice: Subject to any disclaimer, the term of this patent is extended or adjusted under 35 U.S.C. 154(b) by 189 days.

(21) Appl. No.: 12/902,458

(22) Filed: Oct. 12, 2010

(65) Prior Publication Data

US 2011/0083490 A1    Apr. 14, 2011

(30) Foreign Application Priority Data

Oct. 13, 2009  (JP) ................................. 2009-235897
Oct. 4, 2010   (JP) ................................. 2010-224732

(51) Int. Cl.
    *G01N 27/26*         (2006.01)
(52) U.S. Cl.
    USPC ........................... 204/426; 204/421; 204/425
(58) Field of Classification Search
    USPC ......................................... 204/425, 421, 426
    See application file for complete search history.

(56) References Cited

U.S. PATENT DOCUMENTS

2008/0105545 A1*  5/2008  Nakagaki et al. ............. 204/424
2009/0117007 A1   5/2009  Furuta et al.

FOREIGN PATENT DOCUMENTS

| EP | 0 678 740 A1 | 10/1995 |
|----|---|---|
| EP | 1 001 262 A1 | 5/2000 |
| EP | 1 484 604 A2 | 12/2004 |
| EP | 1 486 779 A2 | 12/2004 |
| EP | 1 710 568 A2 | 10/2006 |
| EP | 2 058 652 A1 | 5/2009 |
| EP | 2 105 731 A2 | 9/2009 |
| EP | 2 270 484 A1 | 1/2011 |
| JP | 08-271476 A1 | 10/1996 |
| JP | 2006-284223 A1 | 10/2006 |
| JP | 2009-115618 A1 | 5/2009 |

OTHER PUBLICATIONS

Japanese Office Action dated Feb. 19, 2013.

* cited by examiner

*Primary Examiner* — Luan Van
*Assistant Examiner* — Louis Rufo
(74) *Attorney, Agent, or Firm* — Burr & Brown

(57) ABSTRACT

A gas sensor includes an internal space, diffusion control part, pumping cell, and measuring cell. The diffusion control part communicates with the internal space and has a slit-like shape with a smaller thickness than that of the internal space. The pumping cell pumps out oxygen from the internal space when voltage is applied between a first electrode fowled on a surface of the internal space and a second electrode formed outside the internal space. The measuring cell measures a current flowing between a third and fourth electrodes when a voltage is applied between the third and fourth electrodes. The third electrode is formed in the diffusion control part, and can reduce an oxide gas component in a predetermined gas component to which a predetermined diffusion resistance has been applied by the diffusion control part. The fourth electrode is formed in a part different from the diffusion control part.

10 Claims, 4 Drawing Sheets

GAS SENSOR

BACKGROUND OF THE INVENTION

1. Field of the Invention

The present invention relates to a gas sensor including a sensor element and measuring a predetermined gas component in a measurement gas.

2. Description of Related Art

Conventionally, various measuring apparatuses have been used for recognizing a concentration of a desired gas component in a measurement gas. For example, as a device for measuring a NOx concentration in a measurement gas such as a combustion gas, known is a gas sensor having an electrochemical pumping cell structured by forming a Pt electrode and a Rh electrode on an oxygen-ion conductive solid electrolyte layer, such as a zirconia ($ZrO_2$) layer. In such a gas sensor, an electrode protective layer constituted by a porous body is formed so as to cover a measuring electrode. The electrode protective layer serves to limit the amount of NOx flowing into the measuring electrode, and additionally serves for protecting the measuring electrode.

In a known gas sensor, for example, the electrode protective layer is formed so as to have a sufficient thickness also near ends of the measuring electrode, to thereby effectively prevent an occurrence of cracking or peeling-off of the electrode protective layer, which is caused by a stress generated by repetitive oxidation/reduction of an electrode metal, or the like (for example, see Japanese Patent Application Laid-Open No. 2006-284223).

However, there is the following problem. When the gas sensor as disclosed in Japanese Patent Application Laid-Open No. 2006-284223 is mounted in an exhaust system of an internal combustion engine such as an automobile engine and the internal combustion engine is driven, harmful substances (Mg, Na, Ca, and the like) contained in the exhaust gas may clog the electrode protective layer constituted by the porous body. Such clogging of the electrode protective layer makes it difficult that a measurement gas reaches the measuring electrode, so that the sensitivity of the gas sensor to a measurement gas component such as NOx, in other words, a measurement accuracy, gradually deteriorates along with the use of the gas sensor.

Additionally, in the gas sensor as disclosed in Japanese Patent Application Laid-Open No. 2006-284223, an occurrence of cracking or peeling-off of the electrode protective layer is effectively prevented by devising the structure of the electrode protective layer, but a stress is still applied to the electrode protective layer because of repetitive oxidation/reduction of the electrode metal, or the like. That is, the above-described gas sensor involves a problem that the possibility of an occurrence of cracking or peeling-off of the electrode protective layer increases along with the use, and the measurement accuracy deteriorates due to the occurrence of cracking, peeling-off, or the like, of the electrode protective layer.

SUMMARY OF THE INVENTION

The present invention relates to a gas sensor which measures a predetermined gas component in a measurement gas component, and is particularly directed to a sensor element included in the gas sensor.

According to the present invention, a sensor element of a gas sensor is constituted by an oxygen-ion conductive solid electrolyte as a main component, and including: an internal space to which a measurement gas is introduced from the outside; a diffusion control part in communication with the internal space in a lengthwise direction of the sensor element, the diffusion control part having a slit-like shape with a smaller thickness than that of the internal space, the diffusion control part applying a predetermined diffusion resistance to the measurement gas having been introduced to the internal space; a pumping cell that pumps out oxygen existing in the internal space; and a measuring cell. The pumping cell includes: a first electrode formed on a surface of the internal space; and a second electrode formed in a space different from the internal space. The pumping cell pumps out oxygen existing in the internal space when a predetermined voltage is applied between the first electrode and the second electrode. The measuring cell includes: a third electrode formed in the diffusion control part, the third electrode reducing an oxide gas component in the predetermined gas component to which the predetermined diffusion resistance has been applied by the diffusion control part; and a fourth electrode formed in a part different from the diffusion control part. The measuring cell measures a current flowing between the third electrode and the fourth electrode when a voltage is applied between the third electrode and the fourth electrode.

This realizes a gas sensor in which a measurement accuracy is stably maintained even through repetitive use.

Preferably, a height of the diffusion control part is equal to or more than a film thickness of the third electrode and ten times or less of the film thickness of the third electrode.

This realizes a gas sensor having an improved responsiveness.

It is therefore an object of the present invention to provide a gas sensor in which a measurement accuracy is stably maintained even through repetitive use.

These and other objects, features, aspects and advantages of the present invention will become more apparent from the following detailed description of the present invention when taken in conjunction with the accompanying drawings.

DESCRIPTION OF THE PREFERRED EMBODIMENTS

<Outline Structure of Gas Sensor>

Firstly, an outline of the structure of a gas sensor 100 will be described.

Figure 1:
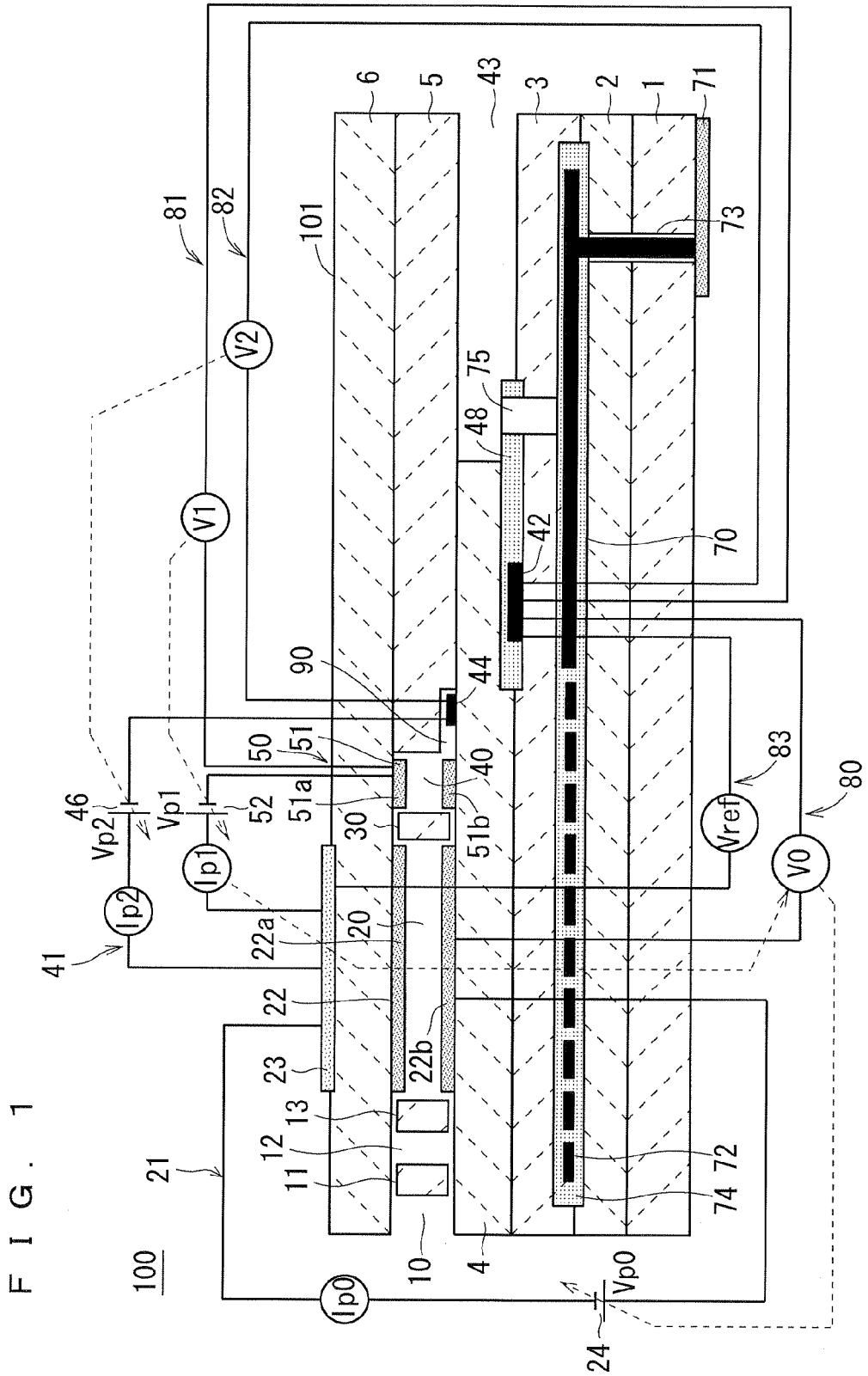
FIG. 1 is a cross-sectional view schematically showing an outline of an exemplified structure of a gas sensor according to a preferred embodiment.

FIG. 1 is a cross-sectional view schematically showing an outline of an exemplified structure of the gas sensor 100. A sensor element 101 is an elongated plate-shaped element having a structure in which six layers, namely, a first substrate layer 1, a second substrate layer 2, a third substrate layer 3, a first solid electrolyte layer 4, a spacer layer 5, and a second solid electrolyte layer 6, are laminated in the mentioned order from the bottom side seen in FIG. 1, each of the layers being formed as an oxygen-ion conductive solid electrolyte layer such as a zirconia ($ZrO_2$) layer. The solid electrolyte forming these six layers is densely airtight. The sensor element 101 is manufactured by, for example, performing a predetermined process and printing a circuit pattern on ceramic green sheets, each of which corresponds to each of the layers, then laminating the green sheets, and furthermore baking the laminated body to integrate it.

Between a lower surface of the second solid electrolyte layer 6 and an upper surface of the first solid electrolyte layer 4 at one end portion of the sensor element 101, a gas inlet 10 a first diffusion control part 11, a buffer space 12, a second diffusion control part 13, a first internal space 20, a third diffusion control part 30, a second internal space 40, and a fourth diffusion control part 90 are adjacently formed in the mentioned order so as to be in communication with one another.

The gas inlet 10, the buffer space 12, the first internal space 20, and the second internal space 40 are spaces within the sensor element 101 provided by hollowing out the spacer layer 5, in which their upper portions are defined by the lower surface of the second solid electrolyte layer 6, their lower portions are defined by the upper surface of the first solid electrolyte layer 4, and their side portions are defined by a side surface of the spacer layer 5.

Each of the first diffusion control part 11, the second diffusion control part 13, and the third diffusion control part 30 is provided as two horizontally long slits (whose openings are elongated in a direction perpendicular to the plane of the drawing sheet of FIG. 1). The fourth diffusion control part 90 is provided as one horizontally long slit (whose opening is elongated in the direction perpendicular to the plane of the drawing sheet of FIG. 1). A part extending from the gas inlet 10 to the second internal space 40 is also referred to as a gas distribution part.

At a position which is farther from the end portion than the gas distribution part is, a reference gas inlet space 43 is provided between an upper surface of the third substrate layer 3 and a lower surface of the spacer layer 5. A side portion of the reference gas inlet space 43 is defined by a side surface of the first solid electrolyte layer 4. As a reference gas for measuring a NOx concentration, for example, air is introduced into the reference gas inlet space 43.

An air introduction layer 48 is constituted by porous alumina. The reference gas is introduced through the reference gas inlet space 43 into the air introduction layer 48. The air introduction layer 48 is formed so as to cover a reference electrode 42.

The reference electrode 42 is an electrode formed so as to be interposed between the upper surface of the third substrate layer 3 and the first solid electrolyte layer 4. As described above, the air introduction layer 48 leading to the reference gas inlet space 43 is provided around the reference electrode 42. By using the reference electrode 42, an oxygen concentration (oxygen partial pressure) in the first internal space 20 or the second internal space 40 can be measured, as will be described later.

In the gas distribution part, the gas inlet 10 is open to the outside, and a measurement gas is taken into the sensor element 101 from the outside through the gas inlet 10.

The first diffusion control part 11 applies a predetermined diffusion resistance to the measurement gas taken through the gas inlet 10.

The buffer space 12 is provided in order to guide the measurement gas introduced from the first diffusion control part 11, to the second diffusion control part 13.

The second diffusion control part 13 applies a predetermined diffusion resistance to the measurement gas introduced from the buffer space 12 into the first internal space 20.

When the measurement gas is introduced from the outside of the sensor element 101 into the first internal space 20, the measurement gas which was abruptly taken into the sensor element 101 through the gas inlet 10 due to a pressure fluctuation of the measurement gas existing in the outside (a pulsation of exhaust gas pressure, in a case where the measurement gas is an automobile exhaust gas) is not directly introduced into the first internal space 20, but is introduced into the first internal space 20 after a concentration fluctuation in the measurement gas is cancelled through the first diffusion control part 11, the buffer space 12, and the second diffusion control part 13. As a result, the concentration fluctuation in the measurement gas introduced into the first internal space 20 is reduced to as small as negligible.

The first internal space 20 is provided as a space for adjusting oxygen partial pressure in the measurement gas introduced through the second diffusion control part 13. The oxygen partial pressure is adjusted by the operation of a main pumping cell 21.

The main pumping cell 21 is an electrochemical pumping cell constituted by an inside pump electrode 22, an outside pump electrode 23, and a part of the second solid electrolyte layer 6 interposed between these electrodes. The inside pump electrode 22 has a ceiling electrode portion 22a provided on a substantially entire part of the lower surface of the second solid electrolyte layer 6 facing the first internal space 20. The outside pump electrode 23 is provided in a region on an upper surface of the second solid electrolyte layer 6 corresponding to the ceiling electrode portion 22a, so as to be exposed to the outside.

The inside pump electrode 22 is formed over the upper and lower solid electrolyte layers (the second solid electrolyte layer 6 and the first solid electrolyte layer 4) which define the first internal space 20, and the spacer layer 5 which provides a side wall to the first internal space 20. To be specific, the ceiling electrode portion 22a is formed on the lower surface of the second solid electrolyte layer 6 which provides a ceiling surface to the first internal space 20. A bottom electrode portion 22b is formed on the upper surface of the first solid electrolyte layer 4 which provides a bottom surface to the first internal space 20. A side electrode portion (not shown) connecting the ceiling electrode portion 22a to the bottom electrode portion 22b is formed on side wall surfaces (inner surfaces) of the spacer layer 5 which forms both side wall portions of the first internal space 20. Thus, the inside pump electrode 22 has a tunnel-like shape at a location where the side electrode portion is disposed.

Each of the inside pump electrode 22 and the outside pump electrode 23 is formed as a porous cermet electrode (for example, a cermet electrode including Pt containing Au by 1% and zirconia). The inside pump electrode 22 which is brought into contact with the measurement gas is formed using a material having a weakened reduction ability with respect to a NOx component in the measurement gas, or having no reduction ability with respect to the NOx component in the measurement gas.

In the main pumping cell 21, a desired pump voltage Vp0 is applied between the inside pump electrode 22 and the outside pump electrode 23 to make a pump current Ip0 flow in a positive direction or a negative direction between the inside pump electrode 22 and the outside pump electrode 23, and this allows oxygen existing within the first internal space 20 to be pumped out to the outside or oxygen existing in the outside to be pumped into the first internal space 20.

In order to detect an oxygen concentration (oxygen partial pressure) in the atmosphere of the first internal space 20, an electrochemical sensor cell, in other words, a main-pump-controlling oxygen-partial-pressure detection sensor cell 80 is formed with the inside pump electrode 22, the second solid electrolyte 6, the spacer layer 5, the first solid electrolyte 4, the third substrate layer 3, and the reference electrode 42.

The oxygen concentration (oxygen partial pressure) in the first internal space 20 can be recognized by measuring an electromotive force V0 of the main-pump-controlling oxygen-partial-pressure detection sensor cell 80. Moreover, the pump current Ip0 is controlled by feedback-controlling Vp0 so as to maintain the electromotive force V0 constant. Thereby, the oxygen concentration in the first internal space 20 can be maintained at a predetermined constant value.

The third diffusion control part 30 applies a predetermined diffusion resistance to the measurement gas whose oxygen concentration (oxygen partial pressure) has been controlled in the first internal space 20 by the operation of the main pumping cell 21, and guides the measurement gas to the second internal space 40.

The second internal space 40 is provided as a space for adjusting oxygen partial pressure in the measurement gas introduced through the third diffusion control part 30. Oxygen partial pressure is adjusted by the operation of an auxiliary pumping cell 50.

In the second internal space 40, the auxiliary pumping cell 50 performs further adjustment of oxygen partial pressure on the measurement gas whose oxygen concentration (oxygen partial pressure) has been controlled in advance in the first internal space 20 and which has then been introduced through the third diffusion control part 30. This enables an oxygen concentration in the second internal space 40 to be accurately maintained constant. Therefore, the gas sensor 100 can measure a NOx concentration with a high accuracy.

The auxiliary pumping cell 50 is an auxiliary electrochemical pumping cell constituted by an auxiliary pump electrode 51, the outside pump electrode 23 (not limited to the outside pump electrode 23 but may be an appropriate electrode positioned outside the sensor element 101), and the second solid electrolyte layer 6. The auxiliary pump electrode 51 has a ceiling electrode portion 51a provided on a substantially entire part of the lower surface of the second solid electrolyte layer 6 facing the second internal space 40.

Similarly to the inside pump electrode 22 provided in the first internal space 20, the auxiliary pump electrode 51 has a tunnel-like shape and provided in the second internal space 40. That is, the ceiling electrode portion 51a is formed on the second solid electrolyte layer 6 which provides a ceiling surface to the second internal space 40. A bottom electrode portion 51b is formed on the first solid electrolyte layer 4 which provides a bottom surface to the second internal space 40. A side electrode portion (not shown) connecting the ceiling electrode portion 51a to the bottom electrode portion 51b is formed on both wall surfaces of the spacer layer 5 which provides side walls to the second internal space 40.

Similarly to the inside pump electrode 22, the auxiliary pump electrode 51 is formed using a material having a weakened reduction ability with respect to a NOx component in the measurement gas, or having no reduction ability with respect to the NOx component in the measurement gas.

In the auxiliary pumping cell 50, a desired voltage Vp1 is applied between the auxiliary pump electrode 51 and the outside pump electrode 23, and this allows oxygen existing in the atmosphere of the second internal space 40 to be pumped out to the outside or oxygen existing in the outside to be pumped into the second internal space 40.

In order to control oxygen partial pressure in the atmosphere of the second internal space 40, an electrochemical sensor cell, in other words, an auxiliary-pump-controlling oxygen-partial-pressure detection sensor cell 81 is formed with the auxiliary pump electrode 51, the reference electrode 42, the second solid electrolyte layer 6, the spacer layer 5, the first solid electrolyte layer 4, and the third substrate layer 3.

A variable power source 52 causes the auxiliary pumping cell 50 to perform pumping. The variable power source 52 is voltage-controlled based on an electromotive force V1 which is detected by the auxiliary-pump-controlling oxygen-partial-pressure detection sensor cell 81. Therefore, the oxygen partial pressure in the atmosphere of the second internal space 40 is lowered to have substantially no influence on the NOx measurement.

At the same time, a pump current Ip1 of the auxiliary pumping cell 50 is used for a control of the electromotive force of the main-pump-controlling oxygen-partial-pressure detection sensor cell 80. Specifically, the pump current Ip1 is inputted as a control signal to the main-pump-controlling oxygen-partial-pressure detection sensor cell 80, and its electromotive force V0 is controlled, so that a gradient of the oxygen partial pressure in the measurement gas introduced through the third diffusion control part 30 into the second internal space 40 is maintained so as to be always constant. When used as a NOx sensor, the oxygen concentration in the second internal space 40 is maintained at a constant value of approximately 0.001 ppm, by the operations of the main pumping cell 21 and the auxiliary pumping cell 50.

The fourth diffusion control part 90 applies a predetermined diffusion resistance suitable for the measurement of a nitrogen oxide (NOx) concentration to the measurement gas introduced from the second internal space 40, and supplies the measurement gas to a measuring pumping cell 41, as will be described later. In the gas sensor 100, the NOx concentration is measured by an operation of the measuring pumping cell 41.

The measuring pumping cell 41 is an electrochemical pumping cell constituted by a measuring electrode 44, the outside pump electrode 23, the second solid electrolyte layer 6, the spacer layer 5, and the first solid electrolyte layer 4. The measuring electrode 44 is provided on the upper surface of the first solid electrolyte layer 4 which forms the fourth diffusion control part 90.

The measuring electrode 44 is a porous cermet electrode. The measuring electrode 44 also functions as a NOx reducing catalyst which reduces NOx existing in the atmosphere of the fourth diffusion control part 90.

The measuring pumping cell 41 can pump out oxygen generated by decomposition of nitrogen oxide in the atmosphere around the measuring electrode 44, and detects the amount of the generated oxygen as a pump current Ip2.

In order to detect oxygen partial pressure around the measuring electrode 44, an electrochemical sensor cell, in other words, a measuring-pump-controlling oxygen-partial-pressure detection sensor cell 82 is formed with the second solid electrolyte layer 6, the spacer layer 5, the first solid electrolyte layer 4, the third substrate layer 3, the measuring electrode 44, and the reference electrode 42. The variable power source 46 is controlled based on an electromotive force V2 detected by the measuring-pump-controlling oxygen-partial-pressure detection sensor cell 82.

The measurement gas introduced into the fourth diffusion control part 90, to which the predetermined diffusion resistance is being applied, reaches the measuring electrode 44. Nitrogen oxide in the measurement gas around the measuring electrode 44 is reduced ($2NO \rightarrow N_2 + O_2$), to generate oxygen.

The generated oxygen is pumped by the measuring pumping cell 41. At this time, a voltage Vp2 of the variable power source is controlled such that a control voltage V2 detected by the measuring-pump-controlling oxygen-partial-pressure detection sensor cell 82 can be maintained constant. The amount of oxygen generated around the measuring electrode 44 is proportional to a nitrogen-oxide concentration in the measurement gas. Thus, the nitrogen-oxide concentration in the measurement gas is calculated by using the pump current Ip2 of the measuring pumping cell 41.

If the measuring electrode 44, the first solid electrolyte layer 4, the third substrate layer 3, and the reference electrode 42 are combined to form an electrochemical sensor cell functioning as oxygen-partial-pressure detection means, an electromotive force can be detected in accordance with a difference between the amount of oxygen generated by the reduction of a NOx component in the atmosphere around the measuring electrode 44 and the amount of oxygen contained in a reference atmosphere. Thereby, a concentration of the NOx component in the measurement gas can be obtained.

An electrochemical sensor cell 83 is formed with the second solid electrolyte layer 6, the spacer layer 5, the first solid electrolyte layer 4, the third substrate layer 3, the outside pump electrode 23, and the reference electrode 42. By an electromotive force Vref obtained by the sensor cell 83, oxygen partial pressure in the measurement gas existing in the outside of the sensor can be detected.

In the gas sensor 100 having the above-described structure, by operating the main pumping cell 21 and the auxiliary pumping cell 50, the measurement gas whose oxygen partial pressure is always maintained at a constant low value (having substantially no influence on the NOx measurement) is given to the measuring pumping cell 41. Accordingly, the NOx concentration in the measurement gas can be recognized based on the pump current Ip2 which flows due to the oxygen generated by the reduction of NOx being pumped out by the measuring pumping cell 41 substantially in proportion to the NOx concentration in the measurement gas.

Furthermore, in order to enhance an oxygen-ion conductivity of the solid electrolyte, the sensor element 101 includes a heater part 70 serving for a temperature control for heating and keeping warm the sensor element 101. The heater part 70 includes a heater electrode 71, a heater 72, a through hole 73, a heater insulating layer 74, and a pressure diffusion hole 75.

The heater electrode 71 is an electrode formed in contact with a lower surface of the first substrate layer 1. By connecting the heater electrode 71 to an external power source, electrical power can be supplied to the heater part 70 from the outside.

The heater 72 is an electric resistor interposed between the second substrate layer 2 and the third substrate layer 3 vertically. The heater 72 is connected to the heater electrode 71 via the through hole 73. The heater 72 generates heat when power is supplied from the outside through the heater electrode 71, and heats and keeps warm the solid electrolyte which forms the sensor element 101.

The heater 72 is buried over the entire area extending from the first internal space 20 to the second internal space 40, so that the temperature of the entire sensor element 101 can be adjusted at a temperature at which the solid electrolyte is activated.

The heater insulating layer 74 is an insulating layer constituted by an insulator such as alumina and formed on upper and lower surfaces of the heater 72. The heater insulating layer 74 is formed for the purpose of providing an electrical insulation between the second substrate layer 2 and the heater 72 and an electrical insulation between the third substrate layer 3 and the heater 72.

The pressure diffusion hole 75 is formed through the third substrate layer 3, and communicates with the reference gas inlet space 43. The pressure diffusion hole 75 is formed for the purpose of relieving a rise in the internal pressure which is involved in a temperature rise in the heater insulating layer 74.

<Configuration of Fourth Diffusion Control Part>

Figure 2:
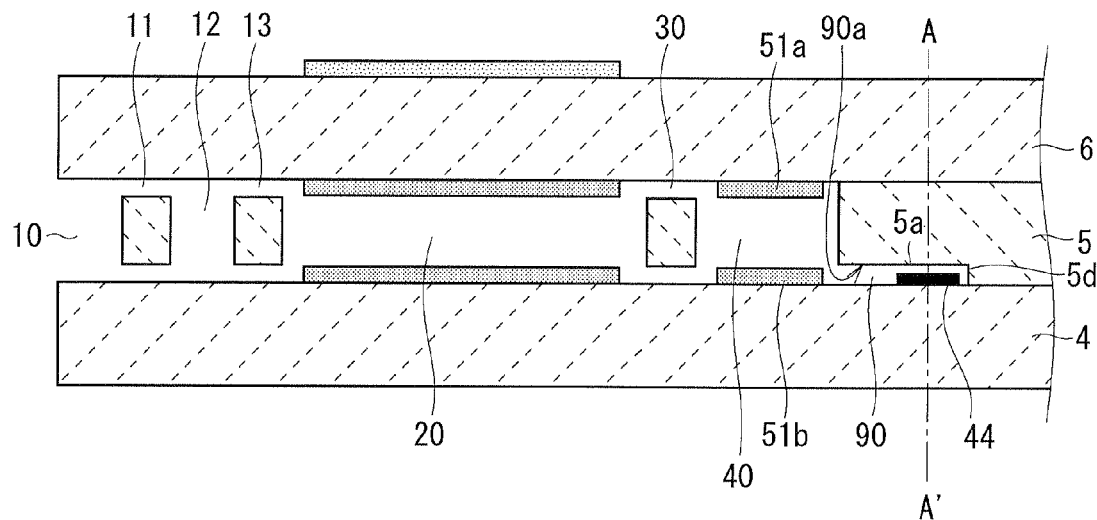
FIG. 2 is a partial cross-sectional view showing an outline of an exemplified structure of the gas sensor according to the preferred embodiment.
Figure 3:
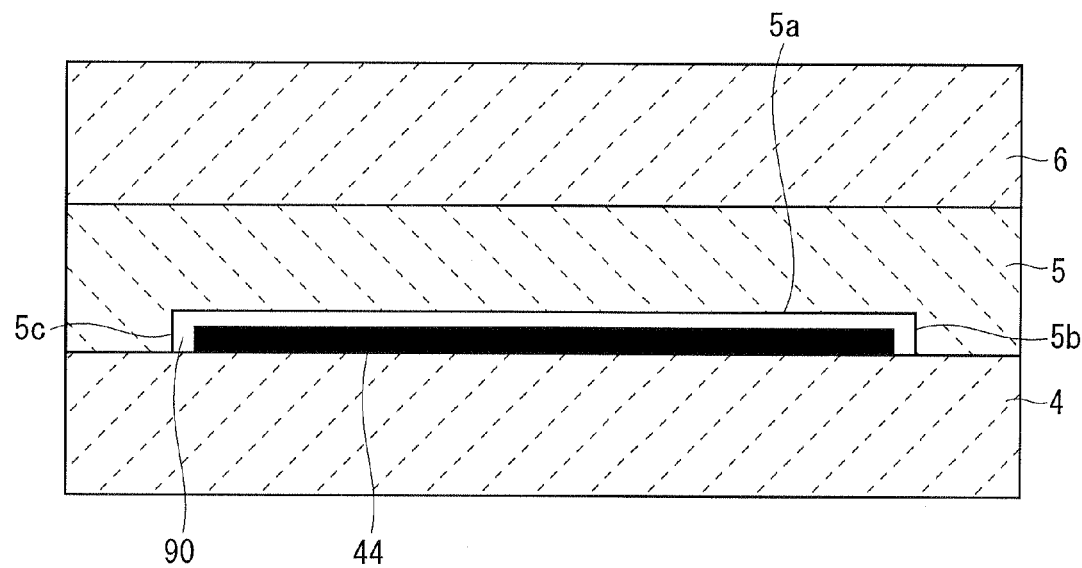
FIG. 3 schematically shows a cross-section of the gas sensor of FIG. 2 taken along the line A-A', as seen from a reference gas inlet space side.

Next, a configuration of the fourth diffusion control part 90 will be described. FIG. 2 is a partial cross-sectional view schematically showing a structure of the sensor element 101 according to this preferred embodiment. FIG. 3 schematically shows a cross-section of the gas sensor 100 of FIG. 2 taken along the line A-A'.

As shown in FIG. 2, the fourth diffusion control part 90 is a space provided by hollowing out the spacer layer 5 so as to communicate with the second internal space 40. The measuring electrode 44 is provided in the fourth diffusion control part 90. However, no electrode protective layer is provided on the measuring electrode 44. That is, the measuring electrode 44 is directly exposed in the fourth diffusion control part 90.

In more detail, as shown in FIGS. 2 and 3, the fourth diffusion control part 90 is provided with an upper portion thereof defined by an inner surface 5a of the spacer layer 5, a side portion thereof defined by inner surfaces 5b to 5d of the spacer layer 5, and a lower portion thereof defined by the upper surface of the first solid electrolyte layer 4. That is, the fourth diffusion control part 90 is provided such that its height (its length with respective to a shorter-side direction in the cross section) is smaller than that of the second internal space 40. As a result, the fourth diffusion control part 90 functions as one horizontally long slit extending in a longer-side direction of the sensor element 101. This structure allows the fourth diffusion control part 90 to apply a predetermined diffusion resistance to the measurement gas introduced from the second internal space 40.

In the fourth diffusion control part 90, it is preferable that a cross-sectional opening area of a portion communicating with the second internal space 40 is 0.005 $mm^2$ or more and 0.3 $mm^2$ or less. Additionally, it is preferable that a distance t from the boundary between the fourth diffusion control part 90 and the second internal space 40 to the end of the measuring electrode 44 at the reference gas inlet space 43 side (the side opposite to the second internal space 40 side) is 0.3 mm or more and 2.0 mm or less (desirably 1.6 mm or less). Moreover, it is preferable that the height of the fourth diffusion control part 90 is equal to or more than a film thickness of the measuring electrode 44 and ten times or less of the film thickness of the measuring electrode 44. In an exemplified case shown in FIG. 2, the inner surface 5a of the spacer layer 5 is flat. However, as long as the above-mentioned cross-sectional opening area is satisfied, the fourth diffusion control part 90 may be configured such that, in the inner surface 5a, a portion 90a (at least a portion under which the measuring electrode 44 is not formed) near the second internal space 40 is brought closer to the upper surface of the first solid electrolyte layer 4, so that a part of the fourth diffusion control part 90 corresponding to this portion has a smaller height than that of the other part. In this preferred embodiment including this case, it is defined that the fourth diffusion control part 90 has a slit-like shape.

The cross-sectional opening area and the distance t in the fourth diffusion control part 90 are appropriately defined in accordance with the degree of the diffusion resistance to be applied to the measurement gas introduced from the second internal space 40.

In the sensor element 101 having such a structure, the measurement gas, which is introduced from the second internal space 40 into the fourth diffusion control part 90 and having the predetermined diffusion resistance applied thereto by the fourth diffusion control part 90, immediately reaches the measuring electrode 44.

Thus, in the gas sensor 100 according to this preferred embodiment, the diffusion resistance of the measurement gas to be supplied to the measuring electrode 44 is controlled in the fourth diffusion control part 90 which is provided instead of an electrode protective layer which would be formed so as to cover the measuring electrode 44 in a conventional gas sensor. Since no electrode protective layer is provided, all the various problems of the conventional gas sensor which are caused by the formation of the electrode protective layer (for example, a problem that harmful substances contained in the measurement gas clog the electrode protective layer, a problem that cracking or peeling-off of the electrode protective layer occurs, and the like) are solved.

Note that, in the gas sensor 100 according to this preferred embodiment, the measurement gas whose oxygen concentration has been controlled by the auxiliary pumping cell 50 does not reach the measuring electrode 44 via an electrode protective layer, but directly reaches the measuring electrode 44. Therefore, harmful substances contained in the measurement gas may be introduced into the fourth diffusion control part 90 and directly reach the measuring electrode 44.

Figure 4:
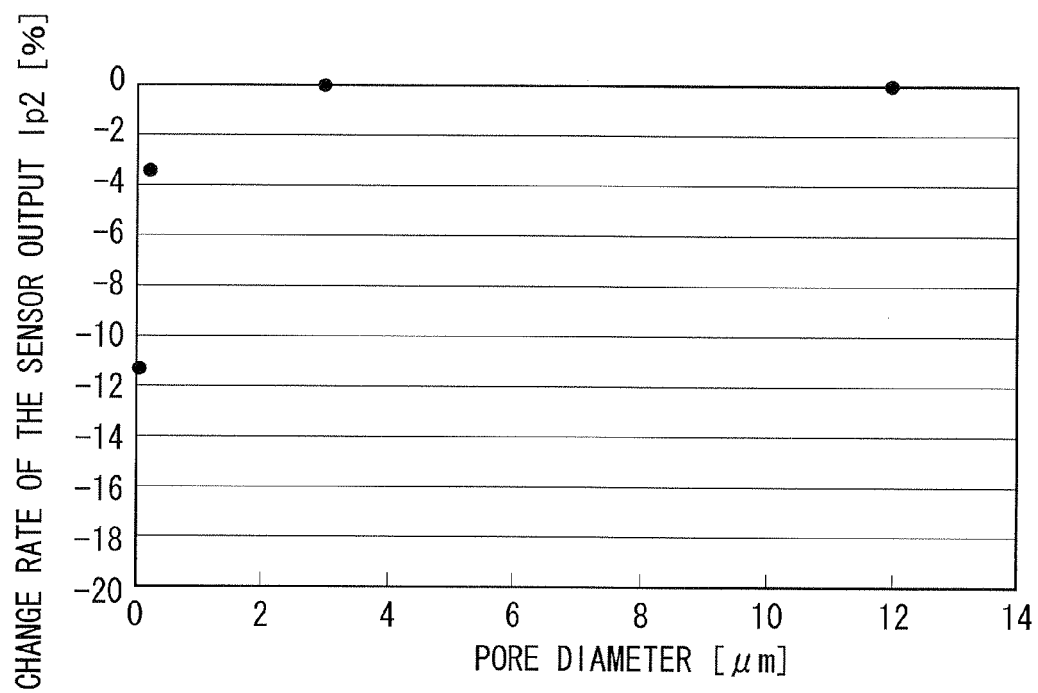
FIG. 4 shows a relationship between a pore diameter in a measuring electrode and a change rate of a sensor output Ip2.

FIG. 4 shows a relationship between a pore diameter in the measuring electrode 44 and a change rate of the sensor output Ip2, which was obtained by performing Mg poisoning tests on various gas sensors different from one another in the pore diameter (average value) of the measuring electrode 44 in order to grasp an influence of such harmful substances (an offset has been made so that the value becomes zero when the pore diameter is 12 μm; see the Example below for details of the Mg poisoning test). From FIG. 4, it can be seen that when the pore diameter is equal to or larger than 3 μm, the sensor output Ip2 is not influenced by the pore diameter in the measuring electrode 44. In the gas sensor 100 according to this preferred embodiment, the measuring electrode 44 is provided in such a manner that the pore diameter is sufficiently larger than 3 μm. Thereby, the harmful substances contained in the measurement gas do not clog the measuring electrode 44 constituted by a porous body, even if the harmful substances contained in the measurement gas reach the measuring electrode 44. Moreover, even if the harmful substances contained in the measurement gas adhere to the measuring electrode 44, substantially no influence is given to oxidation/reduction of an electrode metal.

Thus, the gas sensor 100 according to this preferred embodiment suitably suppresses a deterioration in the measurement accuracy along with the use, which is caused by an occurrence of clogging in an electrode protective layer or cracking or peeling-off of the electrode protective layer. In other words, the measurement accuracy can be stably maintained even through repetitive use.

In addition, when the measuring electrode 44 is formed in the fourth diffusion control part 90 as in this preferred embodiment, the responsiveness of the gas sensor 100 is improved. This is because, since the second internal space 40 is downsized as compared with the conventional gas sensor in which the measuring electrode 44 would be formed in the second internal space 40, the volume of a space to be controlled by the auxiliary pumping cell 50 is reduced to improve a pumping ability (oxygen concentration controllability) of the auxiliary pumping cell 50.

The sensor element 101 having the above-described fourth diffusion control part 90 can be formed in the following method, for example. In the above-described green-sheet process, a predetermined process such as the formation of the second internal space 40 is performed on a ceramic green sheet corresponding to the spacer layer 5. Then, a material with sublimation properties such as theobromine is printed on the ceramic green sheet to thereby form a space serving as the fourth diffusion control part 90. Then, as described above, ceramic green sheets corresponding to the respective layers are laminated and burned, and thus the sensor element 101 in which the fourth diffusion control part 90 is formed is prepared.

As described above, in this preferred embodiment, in the gas sensor 100, the slit-like fourth diffusion control part 90 is provided immediately close to the measuring electrode 44. This can stably maintain the measurement accuracy even through repetitive use, and additionally improve the responsiveness.

EXAMPLE

A gas sensor A which is an example of the gas sensor 100 according to this preferred embodiment and a gas sensor B which is a comparative example were subjected to a Mg poisoning test. The gas sensor B is a conventional gas sensor in which the measuring electrode 44 is provided in the second internal space 40 and covered by an electrode protective layer.

In the Mg poisoning test, a water solution containing ion such as Mg ion was dropped to the vicinity of an end portion of a sensor element and then the gas sensor was driven. This operation was repeatedly performed, and a change rate of a sensor output (Ip2) relative to the amount of dropped water solution was measured. The dropped amount was about 80 μl. The change rate of the sensor output (Ip2) is an index indicative of the degree of a variation in the sensor output (Ip2) which is caused by a difference in the amount of dropped water solution. The change rate of the sensor output (Ip2) is a value represented by a change rate of the sensor output (Ip2) obtained when the water solution is dropped relative to a sensor output obtained when the water solution is not dropped.

In the Mg poisoning test, when a porous body (a measuring electrode or an electrode protective layer) is clogged due to adhering of Mg or the like, the change rate of the sensor output (Ip2) varies. Therefore, by measuring the change rate of the sensor output (Ip2), whether the porous body (the measuring electrode or the electrode protective layer) is clogged by a substance such as Mg or not can be determined.

Figure 5:
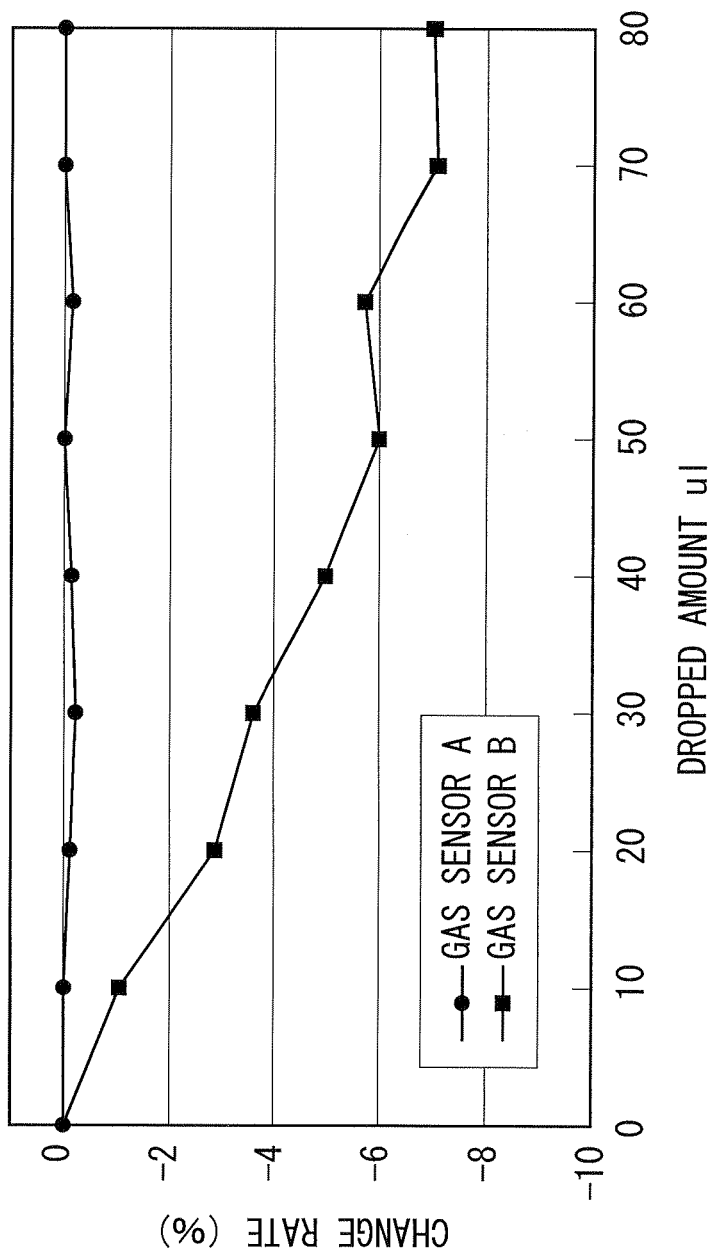
FIG. 5 shows a relationship between the amount of dropped water solution and a change rate of a sensor output.

FIG. 5 shows a result of the Mg poisoning test. As shown in FIG. 5, in the gas sensor A, the change rate was maintained at almost 0% irrespective of the dropped amount. In the gas sensor B, on the other hand, the change rate was lowered as the dropped amount increased. From this result, it can be determined that the porous body was clogged only in the gas sensor B. This result indicates that providing the fourth diffusion control part 90 as in the gas sensor A instead of the electrode protective layer is effective in suppressing the variation in the change rate of the sensor output (Ip2) which is caused by the clogging of the porous body.

As the amount of dropped water solution increases, a driving time (a time of repetitive use) of the gas sensor increases. Therefore, it is considered that the result shown in FIG. 5 also shows a relationship between the driving time of the gas sensor and the change rate of the sensor output (Ip2) under a state where adhering of harmful substances such as Mg to the gas sensor may be continuously occur. In the result shown in FIG. 5, in the gas sensor A, the change rate was almost 0% irrespective of the driving time, whereas in the gas sensor B, the change rate was lowered as the driving time increased. This also means that providing the diffusion control part 90 instead of the electrode protective layer is effective in suppressing the deterioration in the measurement accuracy along with repetitive use.

While the invention has been shown and described in detail, the foregoing description is in all aspects illustrative and not restrictive. It is therefore understood that numerous modifications and variations can be devised without departing from the scope of the invention.

What is claimed is:

1. A gas sensor which has a sensor element constituted by an oxygen-ion conductive solid electrolyte as a main component and detects a predetermined gas component in a measurement gas, said sensor element comprising:
   an internal space to which the measurement gas is introduced from the outside;
   a diffusion control part in communication with said internal space in a lengthwise direction of said sensor element, said diffusion control part forming a slit-like space with a smaller thickness than that of said internal space, said diffusion control part applying a predetermined diffusion resistance to the measurement gas having been introduced to said internal space;
   a pumping cell that pumps out oxygen existing in said internal space; and
   a measuring cell,
   said pumping cell comprising:
      a first electrode formed on a surface of said internal space; and
      a second electrode formed in a space different from said internal space,
      said pumping cell pumping out oxygen existing in said internal space when a predetermined voltage is applied between said first electrode and said second electrode,
   said measuring cell comprising:
      a third electrode formed in said diffusion control part, said third electrode reducing an oxide gas component in said predetermined gas component to which said predetermined diffusion resistance has been applied by said diffusion control part; and
      a fourth electrode formed in a part different from said diffusion control part,
      said measuring cell measuring a current flowing between said third electrode and said fourth electrode when a voltage is applied between said third electrode and said fourth electrode,
   wherein a cross-sectional opening area of a part where said diffusion control part and said internal space communicate with each other is 0.005 mm$^2$ or more and 0.3 mm$^2$ or less, and
   a distance from a boundary between said diffusion control part and said internal space to an end of said third electrode at a side opposite to said internal space is 0.3 mm or more 2.0 mm or less.

2. The gas sensor according to claim 1, wherein
   a height of said diffusion control part is equal to or more than a film thickness of said third electrode and ten times or less of the film thickness of said third electrode.

3. The gas sensor according to claim 1, including a plurality of said internal spaces and a plurality of said pumping cells,
   said plurality of said internal spaces comprising:
      a first internal space to which the measurement gas is introduced from the outside; and
      a second internal space communicating with said first internal space under a predetermined diffusion resistance,
   said plurality of said pumping cells comprising:
      a main pumping cell having said first electrode in said first internal space; and
      an auxiliary pumping cell having said first electrode in said second internal space.

4. The gas sensor according to claim 3, wherein said diffusion control part communicates with said second internal space.

5. The gas sensor according to claim 1, wherein said third electrode is exposed in said diffusion control part.

6. A sensor element of a gas sensor which detects a predetermined gas component in a measurement gas and which is constituted by an oxygen-ion conductive solid electrolyte as a main component, said sensor element comprising:
   an internal space to which the measurement gas is introduced from the outside;
   a diffusion control part in communication with said internal space in a lengthwise direction of said sensor element, said diffusion control part forming a slit-like space with a smaller thickness than that of said internal space, said diffusion control part applying a predetermined diffusion resistance to the measurement gas having been introduced to said internal space;
   a pumping cell that pumps out oxygen existing in said internal space; and
   a measuring cell,
   said pumping cell comprising:
      a first electrode formed on a surface of said internal space; and
      a second electrode formed in a space different from said internal space,
      said pumping cell pumping out oxygen existing in said internal space when a predetermined voltage is applied between said first electrode and said second electrode,
   said measuring cell comprising:
      a third electrode formed in said diffusion control part, said third electrode reducing an oxide gas component in said predetermined gas component to which said predetermined diffusion resistance has been applied by said diffusion control part; and
      a fourth electrode formed in a part different from said diffusion control part,
      said measuring cell measuring a current flowing between said third electrode and said fourth electrode when a voltage is applied between said third electrode and said fourth electrode,
   wherein a cross-sectional opening area of a part where said diffusion control part and said internal space communicate with each other is 0.005 mm$^2$ or more and 0.3 mm$^2$ or less, and
   a distance from a boundary between said diffusion control part and said internal space to an end of said third electrode at a side opposite to said internal space is 0.3 mm or more 2.0 mm or less.

7. The sensor element according to claim 6, wherein
   a height of said diffusion control part is equal to or more than a film thickness of said third electrode and ten times or less of the film thickness of said third electrode.

8. The sensor element according to claim 6, including a plurality of said internal spaces and a plurality of said pumping cells, said plurality of said internal spaces comprise:
- a first internal space to which the measurement gas is introduced from the outside; and
- a second internal space communicating with said first internal space under a predetermined diffusion resistance, said plurality of said pumping cells comprise:
- a main pumping cell having said first electrode in said first internal space; and
- an auxiliary pumping cell having said first electrode in said second internal space.

9. The sensor element according to claim 8, wherein said diffusion control part communicates with said second internal space.

10. The sensor element according to claim 6, wherein said third electrode is exposed in said diffusion control part.

* * * * *